United States Patent [19]
Billington et al.

[11] 3,943,043
[45] Mar. 9, 1976

[54] APPARATUS FOR OR SELECTIVE DISSOLUTION OR DETECTION OF PREDETERMINED METALS

[75] Inventors: Richard W. Billington, London; Robin Drewett, Ascot, both of England

[73] Assignee: Wilkinson Sword Limited, England

[22] Filed: Oct. 9, 1973

[21] Appl. No.: 404,331

[30] Foreign Application Priority Data
Oct. 19, 1972 United Kingdom............... 48167/72

[52] U.S. Cl............ 204/146; 204/129.2; 204/195 R
[51] Int. Cl.[2]....................... C25F 5/00; C25F 3/00
[58] Field of Search ......... 204/195 F, 129.2, 195 R, 204/1 T, 146, 129.55, 140

[56] References Cited
UNITED STATES PATENTS

| | | | |
|---|---|---|---|
| 1,845,231 | 2/1932 | Browning.......................... | 204/129.2 |
| 2,319,196 | 5/1943 | Anderson et al. ................ | 204/129.2 |
| 2,457,234 | 12/1948 | Herbert et al. ................... | 204/129.2 |
| 2,840,521 | 6/1958 | Wasserman...................... | 204/129.2 |
| 3,826,724 | 7/1974 | Riggs, Jr. et al. ................. | 204/146 |

OTHER PUBLICATIONS

New Instrumental Methods in Electrochemistry by Paul Delahay, 1954, pp. 22–23, 286–289, 312–315, 391–407.

*Primary Examiner*—T. M. Tufariello
*Attorney, Agent, or Firm*—Wolfe, Hubbard, Leydig, Voit & Osann, Ltd.

[57] ABSTRACT

Apparatus and methods are disclosed for the selective dissolution of a predetermined metal from, for example, a metal-metal combination. The metal or the metal-metal combination is made the working electrode of an electrolytic cell whose other electrode is electrolytically inert in the cell in use. The working electrode is held at a substantially constant electrical potential relative to a standard calomel electrode, and this potential and the pH of the electrolyte are selected such that the electrical energy passing through the cell during a selected time period is dependent on the amount of the predetermined metal electrolytically dissolved and substantially independent of any other metal which may be present.

14 Claims, 6 Drawing Figures

APPARATUS FOR OR SELECTIVE DISSOLUTION OR DETECTION OF PREDETERMINED METALS

BACKGROUND OF THE INVENTION

The invention relates to methods and apparatus for studying surfaces and more particularly metallic surfaces, and more especially to methods and apparatus for the selective dissolution of a particular metal in conditions in which another metal may also be present.

In one particular example to be described in more detail below, the invention is applied to the determination of the amount of coating material present and/or the porosity of the coating, on a metal surface such as a razor blade edge. However, the invention is by no means limited to such application.

Electrolytic dissolution of metals in electrolytic cells is well known. The use of such techniques, however, for quantitative testing of a metal coating, possibly on another metal, poses problems. As an example, prior techniques have not shown how it may be ensured that only one selected metal is electrolytically dissolved where others may also be present. Furthermore, prior techniques have in general involved equipment which is complex in design and/or use, rendering it unsuitable for application outside the laboratory.

It is an object of the invention to provide improved methods and apparatus for the selective dissolution of a particular metal in conditions in which another metal may also be present.

It is a further object of the invention to provide improved methods and apparatus for studying metal surfaces and which are simple in operation and use so making them available for industrial applications.

BRIEF SUMMARY OF THE INVENTION

According to the invention, there is provided a method of selective dissolution of a predetermined metal, comprising the steps of making the metal at least part of one electrode of an electrolytic cell having another electrode which is electrolytically inert in the cell in use, applying a potential difference of such predetermined magnitude and polarity between the two electrodes that the potential of the said one electrode relative to a standard calomel electrode remains substantially constant, and measuring the electrical energy passing through the cell during a time period which is sufficiently long to substantially dissolve the said metal, the pH of the electrolyte in the cell and the applied potential difference across the cell being selected, with the time period, to ensure electrolytic dissolution of the said predetermined metal but substantially no dissolution of any other metal which may be present at the said one electrode.

According to the invention, there is also provided apparatus for selective dissolution of a predetermined metal, comprising an electrolytic cell containing a predetermined electrolyte, a first electrode in the cell made of material which is electrolytically inert in the electrolyte in use, means for applying a predetermined potential difference of predetermined polarity between the said electrode and a second electrode containing the said metal, the area of the first electrode and the potential difference being such that in use the potential of the second electrode remains substantially constant relative to a standard calomel electrode, means for totalising the energy flowing between the electrodes, and control means for initiating and terminating such totalising, the pH of the electrolyte and the said potential difference being selected to maximise the dissolution of the said predetermined metal relative to any other metal present therewith, and the said control means being adapted to confine the totalising to a time period which is sufficient to allow substantially complete dissolution of the predetermined metal.

DESCRIPTION OF THE DRAWINGS

Apparatus embodying the invention, and methods according to the invention, both for determining the weight of the coating material on the edges of 13% chromium razor blade strip, will now be described, by way of example only, with reference to the accompanying drawings in which.

DESCRIPTION OF PREFERRED EMBODIMENTS

Figure 1:
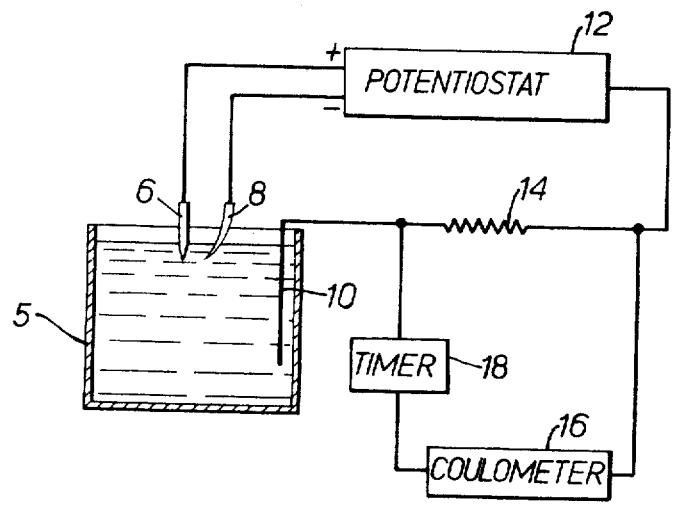
FIG. 1 is a block circuit diagram of apparatus not embodying the invention but shown to explain the operation of the apparatus of FIGS. 2 and 3.

The apparatus shown in FIG. 1 comprises an electrolytic cell 5 containing an electrolyte which in this example is an aqueous 1.17 Normal sodium carbonate solution containing 6.7 volume per cent of saturated sodium bicarbonate solution and having a pH of substantially 11. The chromium-coated edge of the stainless steel razor blade strip to be tested, having an area of about 0.1 cm$^2$, is supported in the electrolyte to form one electrode 6, and the cell has a further, calomel, electrode 8, and a third, platinum, electrode 10. The electrodes 6, 8 and 10 are connected to a potentiostat 12. A resistor 14 is connected in series with the platinum electrode 10, and a coulometer 16 is connected in series with a timer 18 to integrate the current through the platinum electrode 10 during a period of time which is pre-set and controlled by the timer 18 (and in this example may be 20 seconds, say).

In operation, the potentiostat 12 imposes a potential difference between the calomel electrode 8 and the razor blade strip electrode 6, and senses the current flowing between the strip electrode 6 and the platinum electrode 10. In known manner, the potentiostat responds to the sensed current by maintaining the potential difference between the electrodes 6 and 8 constant irrespective of the electrode processes taking place in the cell 5.

For reasons discussed in detail below, the potentiostat is set to maintain a potential difference of 722 millivolts between electrodes 6 and 8, with electrode 6 positive with respect to electrode 8, and the coulometer 16 measures the total quantity of electricity which has flowed through the platinum electrode during the pre-set time. The final reading on the coulometer is found to be the measure of the weight of the chromium coating on the strip 6.

Figure 4:
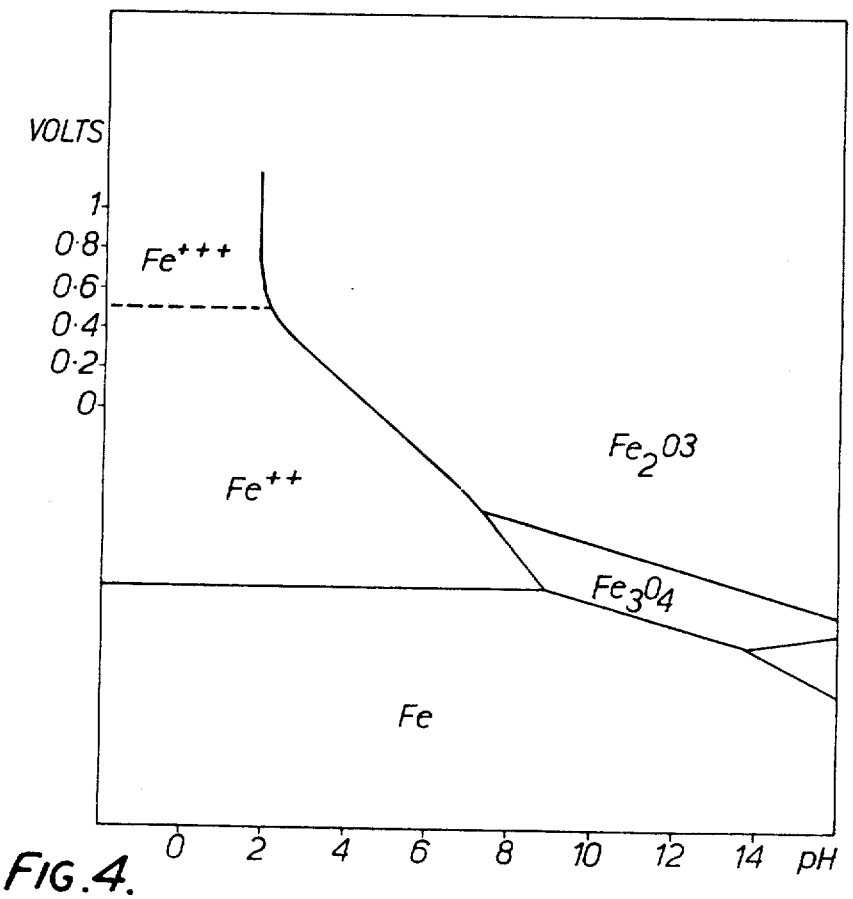
FIGS. 4, 5 and 6 are graphs explaining the operation of the methods and apparatus.
Figure 5:
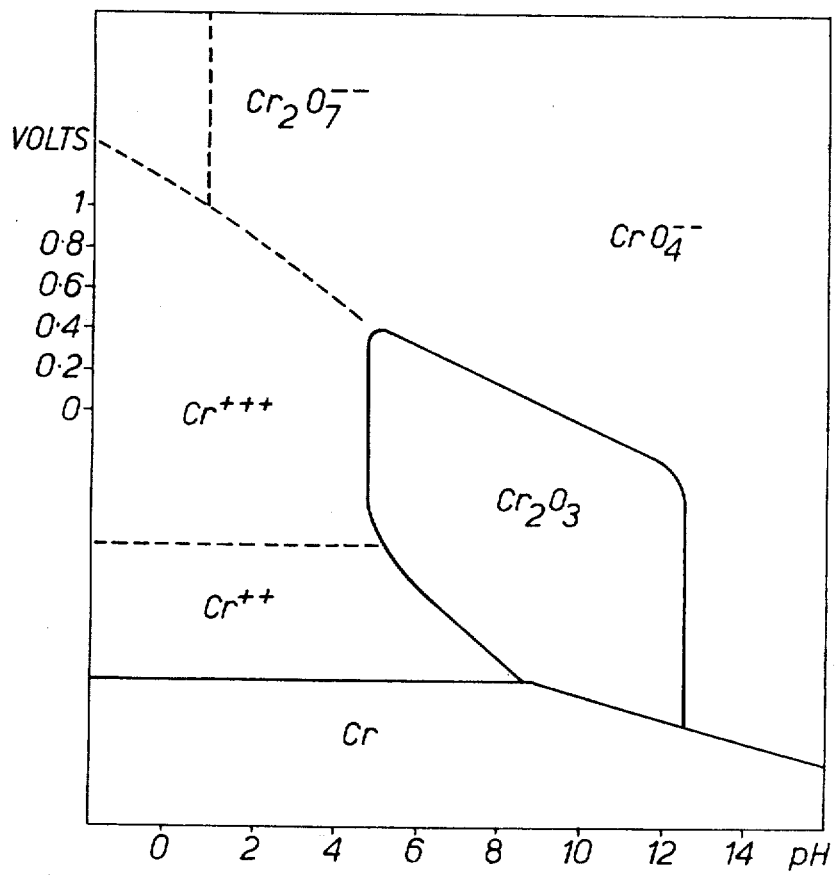

FIGS. 4 and 5 are simplified Pourbaix diagrams for iron (FIG. 4) and chromium (FIG. 5). The diagrams show the thermodynamically stable condition of the metal under various conditions of applied potential (relative to the standard calomel electrode) and pH. If one of these graphs is superimposed on the other, it will be apparent that there is a range of potential values and pH values for which chromium is dissolved but the iron remains passive. Therefore, under these conditions, the electrolytic action taking place in a cell having one electrode combining both chromium and iron would be a function of the weight of chromium present and substantially independent of the iron.

Figure 6:
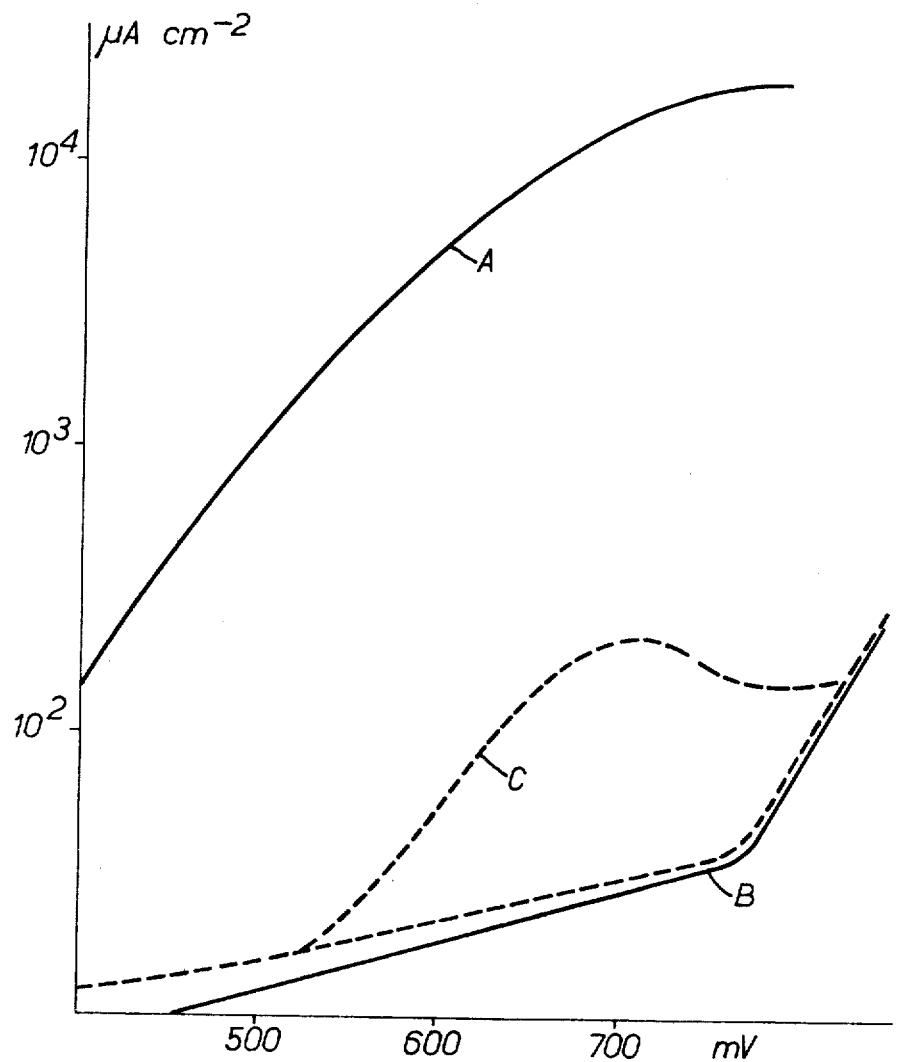

FIG. 6 shows three current/potential scans A, B and C. Scan A is that which would be obtained if electrode 6 in the cell of FIG. 1 were made of chromium and the potential difference between the electrode 6 and the electrode 8 were varied at a suitable rate by means of the potentiostat. Scan B shows the equivalent curve which would be obtained if the electrode 6 were made of iron (with no chromium coating). Scan C is the curve obtained when the electrode 6 is made of 13% chromium stainless steel (with no chromium coating). As shown, chromium dissolves rapidly over the whole potential range shown (400 to 850 mV relative to the standard calomel electrode 8). Tafel behaviour is shown initially, followed by a transition into a limiting current region. The iron (Scan B), however, remains substantially passive over the major proportion of this potential range. The behaviour of the stainless steel (Scan C) is more complex. It remains passive up to about 525 mV (relative to the calomel electrode), then enters a time-dependent transpassive loop. Oxygen evolution does not start until about 775 mV (relative to the standard calomel electrode).

The graphs of FIGS. 4 to 6 indicate that an electrolyte with a pH of above about 4 and an applied potential difference (relative to the standard calomel electrode) between about 400 and 775 mV could provide dissolution of chromium with substantially no effect on iron and relatively little effect on stainless steel. A potential difference towards the upper end of the range, between 525 and 775 mV, say, is advantageous in order to obtain rapid dissolution, and experiment has shown that a pH of about 11 and a potential difference (relative to the standard calomel electrode) of 722 mV gives satisfactory dissolution of chromium in the presence of stainless steel with substantially no effect on the stainless steel (a potential difference of 750 mV relative to the standard calomel electrode gives satisfactory dissolution of chromium in the presence of iron with substantially no effect on the iron). The current efficiency of dissolution under these conditions was found to be 100%.

It therefore follows that if the potentiostat potential in FIG. 1 is set to 722 mV, the total quantity of electricity which has flowed between the coated strip electrode 6 (FIG. 1) and the platinum electrode 10 during a predetermined time is a measure of the amount of chromium involved in the dissolution process, and this quantity is measured by the coulometer 16. The timer 18 is set so that the predetermined time period is sufficient for all the chromium to be dissolved but not to allow any substantial dissolution of the underlying stainless steel. The time period given above (20 seconds) is suitable for a chromium coating thickness of about 200A.

Figure 2:
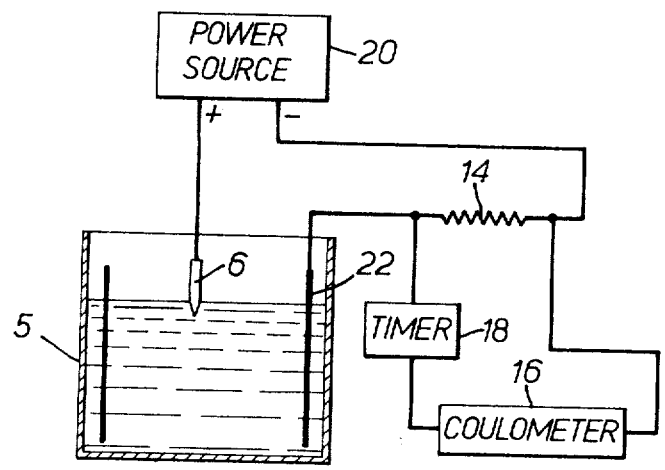
FIG. 2 is a block circuit diagram of a first form of apparatus embodying the invention.

It is found that the role of the potentiostat is to maintain the active electrode (the electrode 6) at the prescribed potential, and that transient voltages are unimportant. In the apparatus of FIG. 2 the potentiostat 12 is replaced by a constant voltage power source 20 set for about 1.0 volts. The electrolytic cell 5 contains the same electrolyte as for the apparatus of FIG. 1, but is modified in that there is no platinum electrode or calomel electrode. Instead, there are merely the strip electrode 6 (of the same area as before) and a counter-electrode 22 which in this example is in the form of a helical strip of 18/8 stainless steel of area approximately 200 sq. cms. The coulometer 16 is connected, through the timer 18, to integrate the current flowing between the electrodes 6 and 22. The timer 18 is set to fix the measurement period at 20 seconds as before.

It is found that with these electrodes and the voltage setting specified, the electrolytic action corresponds with that pertaining in the apparatus of FIG. 1, and the quantity of electricity measured by coulometer 16 represents the coating weight. The stainless steel electrode 22 is substantially inert in the electrolyte and its area is such that it does not enter the limiting current regime. In this way, a substantially potentiostatic control over the electrode 6 is maintained and effectively the potential of the electrode 6 can be said to be maintained at 722 mV with respect to a standard calomel electrode. Conveniently, the resistor 14 can be adjusted to calibrate the coulometer so that the weight of the chromium coating on the strip 6 can be directly read off the coulometer at the end of this period.

Under the conditions pertaining in the instrument, the rate of dissolution of the underlying steel strip 6, although small in relation to that of the chromium, is still finite and makes a small though measurable contribution to the final reading of the coulometer. If the integration period set by the timer 18 is unnecessarily long, then it will include an appreciable time after all the chromium coating has been dissolved, thus increasing the contribution to the final coulometer reading of the steel dissolution current. Therefore if the timer 18 is set at a fixed level chosen to ensure dissolution of all the chromium on a thickly coated edge, the period will be unnecessarily long for a thinly coated edge, giving rise to some inaccuracy.

Figure 3:
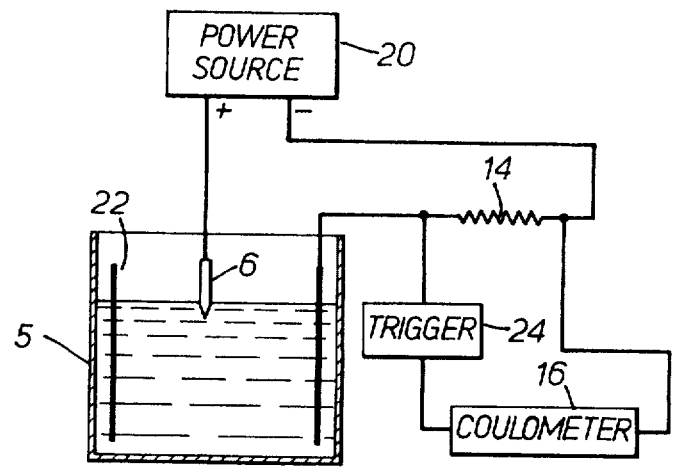
FIG. 3 is a block circuit diagram of a second form of apparatus embodying the invention.

In the apparatus of FIG. 3, which is otherwise the same as that of FIG. 2, the timer 18 is replaced by an electronic trigger device 24 which senses the level of current flowing between the electrodes 6 and 22 and switches the coulometer 16 out of circuit when the current level has fallen to a prescribed value.

The current decays when chromium dissolution has been completed, and it has been found by experiment that the current always decays to about the same background level irrespective of the amount of chromium. The trigger 24 is therefore set to switch off the coulometer 16 when the current has fallen to this level (which is about 0.75 mA per square centimeter of the electrode 6), and the total quantity of electricity measured by the coulometer up to the time of switch off is therefore a measure of the amount of chromium dissolved and is substantially independent of the effect of steel dissolution.

Although the various forms of apparatus, and their methods of operation, have been described in relation to the determination of the weight of chromium coating on stainless steel, it will be appreciated that the apparatus and methods can be used for the determination of chromium coatings on other materials or of other coatings on other or similar materials using the same principle of operation, and adjusting the type of pH of the electrolyte, the preset voltage applied across the cell, the material of the counter-electrode 22, and the period of the timer 18 or the preset triggering level of the trigger 24 as appropriate. The parameters for the method would be established in the same way as those described above for chromium on stainless steel. In particular, the pH of the cell and the preset voltage applied across the cell would be determined by correlating the Pourbaix diagrams and the current/potential scans for the two metals so as to give an idea of the applicable ranges of these two parameters, the optimum values then being selected.

For example, the potentiostat potential for testing chromium on iron would be about 750mv as stated above. For testing chromium on nickel the potentiostat potential would be about 650mv. The equivalent power source voltages for the form of apparatus shown in FIGS. 2 and 3 would be 1.03 volts for chromium on iron and 0.9 volts for chromium on nickel. The same electrolyte and counter-electrode would be used, and a time period (for the apparatus of FIGS. 1 and 2) of 20 seconds would be suitable for coating thicknesses of about 200 A on an area of about 0.1 cm$^2$.

For testing tin coatings on iron, a potentiostat potential of −980 mV (that is, having reversed polarity relative to the calomel electrode compared with the potentials stated above) would be suitable, with an equivalent power source voltage (for the apparatus of FIGS. 2 and 3) of 0.30 volts. These voltages would also be suitable for testing zinc coatings on iron. In these two cases, a suitable electrolyte would be 10% potassium hydroxide. A time period (for the apparatus of FIGS. 1 and 2) of 20 seconds would be suitable for testing tin coatings of about 300 A thickness over an area of 0.1 cm$^2$.

The "potentiostat potentials" of 750 mV, 650 mV and −980 mV referred to above are, like the potential of 722 mV referred to earlier, the potential of the electrode 6 (in the apparatus of FIG. 1, FIG. 2 or FIG. 3) relative to a standard calomel electrode.

In some applications it will be impracticable to immerse the specimen in the cell. In these cases a small area of the specimen may be made the base of the cell, and the cell should contain as small a quantity of electrolyte as possible. As a consequence of the relative reaction rates at the two electrodes, it is necessary that the counter-electrode is the larger (to prevent it entering the limiting-current regime where large changes in electrode potential can be caused by small changes in applied current), and its size largely determines the cell size. The cell size can be reduced by increasing the relative reaction rate at the counter-electrode. Instead of stirring the electrolyte, which is a conventional manner of doing this, a suitable electro-reducible species may be added to the electrolyte. Thus, in the particular case of the determination of chromium on stainless steel described above, an addition of 5% by weight of an oxidising agent such as potassium ferricyanide or potassium bromate allowed an approximately twelve-fold reduction in the area of the counter-electrode. This is merely an example of a suitable reducible species. The ideal requirements of the added species are (a) it should have no influence on the anodic dissolution of the coating or substrate, (b) it should not be oxidized at the anode, and (c) it should provide a cathodic reaction with a high limiting-current density and a low Tafel slope. Potassium ferricyanide and potassium bromate largely meet these criteria with the exception of the Tafel slope. The Tafel slope can be changed by selection of another suitable material for the counter-electrode, and aluminum may be advantageous under certain circumstances.

The apparatus described is advantageous in that it is suitable for use on discontinuous, damaged or uneven coatings. It has a high speed of operation, and is applicable to various coating/substrate combinations and in particular to thin coatings. It will be apparent that the apparatus is not a constant current device.

The principle could also be used in reverse for the determination of coating porosity. In such an application, the electrolyte pH value and the voltage applied across the cell would be set to be appropriate for the underlying substrate rather than the coating material. The final reading of the coulometer 16 would then be a measure of the coating porosity rather than the weight of the coating.

It will be apparent that the apparatus described is in no way limited to the detection of coatings on razor blade edge; that is merely one example of a suitable application. It may be used in many other applications where it is desired to detect films or coatings on other metal surfaces. When used for detecting coatings on razor blade strip edges, it is not limited to the types of razor blade strip referred to above but may be applied to razor blade strip made of other materials.

The apparatus and methods are not, however, limited to the detection of films or coatings. Since the apparatus and methods are designed for the selective dissolution of a particular metal, it will be apparent that they can, for example, be used for the study of surface concentration — for the selective dissolution of one metal present with another in a surface layer. Thus, the method and apparatus can be used to determine the extent of enrichment, at the surface layer, of one metal in an alloy as a result of heat treatment, pickling, polishing or other conventional treatment processes.

It is also possible to use the methods and apparatus described for detecting a selected metal through a porous non-metallic coating thereover so as to determine the porosity of the coating.

What we claim is:

1. Apparatus for selective dissolution of a predetermined metal which is present with at least one other metal in a metal-metal combination as a first electrode in an electrolytic cell, comprising a predetermined electrolyte in the electrolytic cell,
one other electrode, only, mounted in the cell and made of material which is electrolytically inert in the electrolyte in use,
means connected to the electrodes and applying a predetermined potential difference of predetermined polarity between the two electrodes,
means connected to the electrodes for totalising the electrical energy flowing between them in response to the applied potential difference, and
control means for initiating and terminating such totalizing,
the pH of the electrolyte, the said potential difference, and the material of the said other electrode being selected to hold the first electrode at such potential relative to a standard calomel electrode as lies in those areas of the Pourbaix diagrams for the metals where the said predetermined metal is dissolved and the other metal remains passive,
the size of the area of the said other electrode being such that the electrode does not enter the limiting current regime in use, and
the said control means being adapted to confine the totalizing to a time period which is sufficient to allow substantially dissolution of the predetermined metal.

2. Apparatus according to claim 1, in which the said control means includes timing means arranged to hold the energy totalizing means activated for a predetermined and fixed time duration.

3. Apparatus according to claim 1, in which the control means comprises means connected to the electrodes and responsive to the level of current flowing between the electrodes to terminate the energy measurement when the current level has fallen to a predetermined value indicative of substantially complete dissolution of the said predetermined metal.

4. Apparatus according to claim 1 for use where the said predetermined metal is chromium, in which
the pH of the electrolyte is substantially 11, and
the predetermined potential difference applied between the electrodes is such that the potential of the chromium is substantially +722mV with respect to a standard calomel electrode.

5. Apparatus according to claim 4, in which the said electrolyte is an aqueous sodium carbonate solution, substantially 1.17 Normal, containing 6.7 volume percent of saturated sodium bicarbonate.

6. Apparatus according to claim 1 for use where the said predetermined metal is chromium and is present with nickel, in which
the pH of the electrolyte is substantially 11, and
the predetermined potential difference is such that the potential of the chromium is 650 mV with respect to a standard calomel electrode.

7. Apparatus according to claim 1 for use where the said predetermined metal is chromium and is present with iron, in which
the pH of the electrolyte is substantially 11, and
the predetermined potential difference is such that the potential of the chromium is substantially +750 mV with respect to a standard calomel electrode.

8. Apparatus according to claim 1 for use where the said predetermined metal is tin and is present with iron, in which the pH of the electrolyte is substantially 11, and
the predetermined potential difference is such that the potential of the tin is substantially −980 mV with respect to a standard calomel.

9. A method according to claim 1 for use where the the said predetermined metal is zinc and is present with iron, in which
the pH of the electrolyte is substantially 13, and
the predetermined potential difference is such that the potential of the zinc is substantially −980 mV with respect to a standard calomel electrode.

10. Apparatus according to claim 1, in which the electrolyte includes an electro-reducible substance having substantially no influence on the anodic dissolution of the said metal and not being oxidisable at the anode of the cell, to increase the relative reaction rate at the said other electrode.

11. Apparatus for determining the amount of coating material present on the edge of a chromium-coated stainless steel razor blade strip forming a first electrode in an electrolytic cell, comprising
an electrolyte having a pH of substantially 11 in the electrolytic cell,
one other electrode, only, mounted in the cell and made of material which is substantially inert in the electrolyte in use,
an electrical power source connected to the electrodes for applying a predetermined electrical potential difference between the electrodes with the first electrode maintained positive with respect to the other electrode,
energy totalizing means connected to the electrodes to measure the electrical energy which passes between them when the totalizing means is activated, and
control means for controlling the time duration for which the energy totalizing means is activated such that the time duration is sufficient for dissolution of the said chromium coating to be substantially complete, the area of said other electrode being sufficiently great to ensure that the electrode does not enter a limiting current regime in use and the predetermined potential difference being such that the potential of the first electrode is held substantially at a constant value lying between 525 and 750 mV with respect to a standard calomel electrode.

12. Apparatus according to claim 11, in which the said potential difference is substantially 722 mV.

13. Apparatus according to claim 11, in which the control means comprises timing means arranged to hold the energy totalizing means activated for a predetermined and fixed time duration.

14. Apparatus according to claim 11, in which the control means comprises means connected to the said electrodes to be responsive to the level of current flowing between the electrodes to de-activate the totalizing means when the current level has fallen to a predetermined value indicative of substantially complete dissolution of the said predetermined metal.

\* \* \* \* \*